United States Patent [19]

Comings

[11] Patent Number: 5,260,196
[45] Date of Patent: Nov. 9, 1993

[54] METHOD FOR THE DIAGNOSIS OF TOURETTE SYNDROME AND ASSOCIATED DISORDERS

[75] Inventor: David E. Comings, Duarte, Calif.

[73] Assignee: City of Hope, Duarte, Calif.

[21] Appl. No.: 715,660

[22] Filed: Jun. 14, 1991

Related U.S. Application Data

[63] Continuation-in-part of Ser. No. 125,577, Nov. 25, 1987, abandoned, and a continuation-in-part of Ser. No. 271,653, Nov. 16, 1988, and a continuation-in-part of Ser. No. 410,831, Sep. 22, 1989, abandoned, and a continuation-in-part of Ser. No. 562,596, Aug. 3, 1990.

[51] Int. Cl.⁵ .......................... C12Q 1/26; A61K 37/50
[52] U.S. Cl. ....................................... 435/25; 424/94.4
[58] Field of Search ............... 435/6, 189, 25; 536/27, 536/23.5; 935/77, 78; 530/350, 846; 424/94.4

[56] References Cited

PUBLICATIONS

White et al., Principles of Biochemistry, 6th Edition, 1978, p. 750.
Schmid et al. (1982), Embo J, vol. 1, pp. 1287–1293.
Matsubara, Proc. Natl. Acad. Sci., vol. 83, 1986, pp. 6543–6547.
Fritsch et al., Cell, vol. 19, 1980, pp. 959–972.
Mangoni, Adv. in Bio. Psychopharm, 1974, pp. 293–298.

*Primary Examiner*—Margaret Moskowitz
*Assistant Examiner*—Mindy B. Fleisher
*Attorney, Agent, or Firm*—Edward S. Irons

[57] ABSTRACT

Differences in the rate of kynurenine formation in the lysates of red blood cells of a patient suspected of having Tourette syndrome, Tourette syndrome associated disorders or Tourette spectrum disorders and of a control are used for the diagnosis of such disorders.

1 Claim, 21 Drawing Sheets

HUMAN LIVER cDNA LIBRARY IN gt I I (30,000 plaques/filter)
HYBRIDIZED WITH RAT LIVER
TRYPTOPHAN OXYGENASE cDNA CLONE (SCHMID et al, 1982)

```
  1    acctccgtgc ttctcagaca gtgccttttc
       tggaggcacg aagagtctgt cacggaaaag met ser gly cys pro phe leu gly ans
 31    acc ATG AGT GGG TGC CCA TTT TTA GGA AAC
       tgg TAC TCA CCC ACG GGT AAA AAT CCT TTG asn phe gly tyr thr phe lys lys leu pro
 61    AAC TTT GGA TAT ACT TTT AAA AAA CTC CCC
       TTG AAA CCT ATA TGA AAA TTT TTT GAG GGG val glu gly ser glu glu asp lys ser gln
 91    GTA GAA GGC AGC GAA GAA GAC AAA TCA CAA
       CAT CTT CCG TCG CTT CTT CTG TTT AGT GTT thr gly val asn arg ala ser lys gly gly
121    ACT GGT GTG AAT AGA GCC AGC AAA GGA GGT
       TGA CCA CAC TTA TCT CGG TCG TTT CCT CCA leu ile tyr gly asn tyr leu his leu glu
151    CTT ATC TAT GGG AAC TAC CTG CAT TTG GAA
       GAA TAG ATA CCC TTG ATG GAC GTA AAC CTT lys val leu asn ala gln glu leu gln ser
181    AAA GTT TTG AAT GCA CAA GAA CTG CAA AGT
       TTT CAA AAC TTA CGT GTT CTT GAC GTT TCA glu thr lys gly asn lys ile his asp glu
211    GAA ACA AAA GGA AAT AAA ATC CAT GAT GAA
       CTT TGT TTT CCT TTA TTT TAG GTA CTA CTT his leu phe ile ile thr his gln ala tyr
241    CAT CTT TTT ATC ATA ACT CAT CAA GCT TAT
       GTA GAA AAA TAG TAT TGA GTA GTT CGA ATA glu leu trp phe lys gln ile leu trp glu
271    GAA CTC TGG TTT AAG CAA ATC CTC TGG GAG
       CTT GAG ACC AAA TTC GTT TAG GAG ACC CTC leu asp ser val arg glu ile phe gln asn
301    TTG GAT TCT GTT CGA GAG ATC TTT CAG AAT
       AAC CTA AGA CAA GCT CTC TAG AAA GTC TTA gly his val arg asp glu arg asn met leu
331    GGC CAT GTC AGA GAT GAA AGG AAC ATG CTT
       CCG GTA CAG TCT CTA CTT TCC TTG TAC GAA lys val val ser arg met his arg val ser
361    AAG GTT GTT TCT CGG ATG CAC CGA GTG TCA
       TTC CAA CAA AGA GCC TAC GTG GCT CAC AGT val ile leu lys leu leu val gln gln phe
391    GTG ATC CTG AAA CTG CTG GTG CAG CAG TTT
       CAC TAG GAC TTT GAC GAC CAC GTC GTC AAA ser ile leu glu thr met thr ala leu asp
421    TCC ATT CTG GAG ACG ATG ACA GCC TTG GAC
       AGG TAA GAC CTC TGC TAC TGT CGG AAC CTG
```

FIG. 5-1

```
      phe asn asp phe arg glu tyr leu ser pro
451   TTC AAT GAC TTC AGA GAG TAC TTA TCT CCA
      AAG TTA CTG AAG TCT CTC ATG AAT AGA GGT ala ser gly phe gln ser leu gln phe arg
481   GCA TCA GGC TTC CAG AGT TTG CAA TTC CGA
      CGT AGT CCG AAG GTC TCA AAC GTT AAG GCT leu leu glu asn lys ile gly val leu gln
511   CTA TTA GAA AAC AAG ATA GGT GTT CTT CAG
      GAT AAT CTT TTG TTC TAT CCA CAA GAA GTC asn met arg val pro tyr asn arg arg his
541   AAC ATG AGA GTC CCT TAT AAC AGA AGA CAT
      TTG TAC TCT CAG GGA ATA TTG TCT TCT GTA tyr arg asp asn phe lys gly glu glu asn
571   TAT CGT GAT AAC TTC AAA GGA GAA GAA AAT
      ATA GCA CTA TTG AAG TTT CCT CTT CTT TTA glu leu leu leu lys ser glu gln glu lys
601   GAA CTG CTA CTT AAA TCT GAG CAG GAA AAG
      CTT GAC GAT GAA TTT AGA CTC GTC CTT TTC thr leu leu glu leu val glu ala trp leu
631   ACA CTT CTG GAA TTA GTG GAG GCA TGG CTG
      TGT GAA GAC CTT AAT CAC CTC CGT ACC GAC glu arg thr pro gly leu glu pro his gly
661   GAA AGA ACT CCA GGT TTA GAG CCA CAT GGA
      CTT TCT TGA GGT CCA AAT CTC GGT GTA CCT phe asn phe trp gly lys leu glu lys lys
691   TTT AAC TTC TGG GGA AAG CTT GAA AAA AAA
      AAA TTG AAG ACC CCT TTC GAA CTT TTT TTT tyr his gln arg pro gly arg gly ile
721   TAT CAC CAG AGG CCT GGA AGA GGA ATT C
      ATA GTG GTC TCC GGA CCT TCT CCT TAA G
```

FIG. 5-2

```
  1      acctccgtgc ttctcagaca gtgccttttc 1 met ser gly cys pro phe leu gly asn
 31      acc ATG AGT GGG TGC CCA TTT TTA GGA AAC 10      asn phe gly tyr thr phe lys lys leu pro
 61      AAC TTT GGA TAT ACT TTT AAA AAA CTC CCC 20      val glu gly ser glu glu asp lys ser gln
 91      GTA GAA GGC AGC GAA GAA GAC AAA TCA CAA 30      thr gly val asn arg ala ser lys gly gly
121      ACT GGT GTG AAT AGA GCC AGC AAA GGA GGT 40      leu ile tyr gly asn tyr leu his leu glu
151      CTT ATC TAT GGG AAC TAC CTG CAT TTG GAA 50      lys val leu asn ala gln glu leu gln ser
181      AAA GTT TTG AAT GCA CAA GAA CTG CAA AGT 60      glu thr lys gly asn lys ile his asp glu
211      GAA ACA AAA GGA AAT AAA ATC CAT GAT GAA 70      his leu phe ile ile thr his gln ala tyr
241      CAT CTT TTT ATC ATA ACT CAT CAA GCT TAT 80      glu leu trp phe lys gln ile leu trp glu
271      GAA CTC TGG TTT AAG CAA ATC CTC TGG GAG 90      leu asp ser val arg glu ile phe gln asn
301      TTG GAT TCT GTT CGA GAG ATC TTT CAG AAT 100      gly his val arg asp glu arg asn met leu
331      GGC CAT GTC AGA GAT GAA AGG AAC ATG CTT 110      lys val val ser arg met his arg val ser
361      AAG GTT GTT TCT CGG ATG CAC CGA GTG TCA 120      val ile leu lys leu leu val gln gln phe
391      GTG ATC CTG AAA CTG CTG GTG CAG CAG TTT 130      ser ile leu glu thr met thr ala leu asp
421      TCC ATT CTG GAG ACG ATG ACA GCC TTG GAC 140      phe asn asp phe arg glu tyr leu ser pro
451      TTC AAT GAC TTC AGA GAG TAC TTA TCT CCA 150      ala ser gly phe gln ser leu gln phe arg
481      GCA TCA GGC TTC CAG AGT TTG CAA TTC CGA 160      leu leu glu asn lys ile gly val leu gln
511      CTA TTA GAA AAC AAG ATA GGT GTT CTT CAG 170      asn met arg val pro tyr asn arg arg his
541      AAC ATG AGA GTC CCT TAT AAC AGA AGA CAT 180      tyr arg asp asn phe lys gly glu glu asn
571      TAT CGT GAT AAC TTC AAA GGA GAA GAA AAT 190      glu leu leu leu lys ser glu gln glu lys
601      GAA CTG CTA CTT AAA TCT GAG CAG GAA AAG
```

FIG. 5A-1

```
200    thr leu leu glu leu val glu ala trp leu
631    ACA CTT CTG GAA TTA GTG GAG GCA TGG CTG 210    glu arg thr pro gly leu glu pro his gly
661    GAA AGA ACT CCA GGT TTA GAG CCA CAT GGA 220    phe asn phe trp gly lys leu glu lys lys
691    TTT AAC TTC TGG GGA AAG CTT GAA AAA AAA 230    tyr his gln arg pro gly arg      - 236
721    TAT CAC CAG AGG CCT GGA AGA (G)  - 741

237    ile arg ile gln ala lys glu glu ser glu
742    ATA AGG ATT CAG GCT AAA GAA GAG TCT GAA 247    glu lys glu glu gln val ala glu phe gln
772    GAA AAA GAG GAA CAG GTG GCT GAA TTT CAG 257    lys gln lys glu val leu leu ser leu phe
802    AAG CAA AAA GAG GTG CTA CTG TCC TTA TTT 267    asp glu lys arg his glu his leu leu ser
832    GAT GAG AAA CGT CAT GAA CAT CTC CTT AGT 277    lys gly glu arg arg leu ser tyr arg ala
862    AAA GGT GAA AGA CGG CTG TCA TAC AGA GCA 287    leu gln gly ala leu met ile tyr phe tyr
892    CTT CAG GGA GCA TTG ATG ATA TAT TTT TAC 287    arg glu glu pro arg phe gln val pro phe
922    AGG GAA GAG CCT AGG TTC CAG GTG CCT TTC 297    ser leu ala asp phe ser tyr gly his arg
952    AGT TTA GCT GAC TTC TCT TAT GGA CAT AGA 307    phe thr asp asp gln trp arg ile TER pro
982    TTC ACT GAT GAC CAA TGG AGA ATA TAA CCA 317    cys gly met val his arg ile val gly ser
1022   TGT GGC ATG GTG CAC AGA ATC GTG GGC AGC 327    lys ala gly thr gly gly ser ser gly tyr
1052   AAA GCT GGC ACC GGT GGT TCC TCA GGC TAT 337    his tyr leu arg ser thr val ser asp arg
1082   CAC TAC CTG CGA TCA ACT GTG AGT GAT AGG 347    tyr lys val phe val asp leu phe asn leu
1112   TAC AAG GTA TTT GTA GAT TTA TTT AAT CTT 357    ser thr tyr leu ile pro arg his trp ile
1142   TCA ACA TAC CTG ATT CCC CGA CAC TGG ATA 367    pro lys met asn pro thr ile his lys phe
1172   CCG AAG ATG AAC CCA ACC ATT CAC AAA TTT 377    leu tyr thr ala glu tyr cys asp arg leu
1202   CTA TAT ACA GCA GAA TAC TGT GAT AGA TTA
```

FIG. 5A-2

| | | | | | | | | | |
|---|---|---|---|---|---|---|---|---|---|
| 387 | lys | ser | ser | ala | lys | ser | met | lys | asn | thr |
| 1232 | AAA | TCG | TCT | GCA | AAA | TCT | ATG | AAG | AAT | ACT |
| 397 | gly | phe | thr | ala | tyr | phe | leu | phe | ser | met |
| 1262 | GGT | TTC | ACA | GCC | TAT | TTT | TTA | TTT | TCT | ATG |
| 407 | asp | phe | his | lys | tyr | ser | leu | asn | ile | cys |
| 1292 | GAT | TTT | CAT | AAA | TAC | AGT | TTG | AAT | ATA | TGT |
| 417 | met | his | ile | leu | phe | ser | thr | thr | met | leu |
| 1322 | ATG | CAT | ATA | TTG | TTC | AGC | ACC | ACG | ATG | CTC |
| 427 | TER |
| 1352 | tga ttt aat tct aga aac aat ttg att acc |
| 1382 | tct tgt ttg tga caa gac taa gca tta aga |
| 1412 | tga gaa aga ata cat tta aat agt aac att |
| 1442 | gta cat agg gtg ttt tcc tat taa aaa tca |
| 1472 | gtt tcc cct gag act taa tgt aac cac tta |
| 1502 | atg taa tca cta tct cat tgt ttc atc ttt |
| 1532 | ata aac ttg taa act cat cta ttt caa ata |
| 1662 | ttt tat gca gta cat tat att att ctg tac |
| 1692 | aaa ggc ttt caa aca aaa ttt tta aaa taa |
| 1622 | taa agt att aat ctt tca aaa aaa aaa aaa |
| 1652 | aaa aaa |

FIG. 5A-3

```
  1  AACAGGGTAG GATATCTTTG AAAAACTTAT CTATGGAAGA
 41  CAATGAAGAA GACGGAGCTC AAACTGGTGT AAACAGAGCC
 81  AGCAAAGGAG GACTTATCTA TGGGGACTAC TTGCAGTTGG
121  AGAAGATTTT GAATGCACAA GAACTTCAAA GTGAAATCAA
161  AGGGAATAAA ATCCACGACG AGCACCTCTT TATTATAACT
201  CACCAAGCTT ATGAACTTTT GGTTTAAACA AATTCTCTGG
241  GAACTTTGAT TCTGTTCGTG AGATTTTTCA AAATGGCCAA
281  TGTCAGGGAT GAGAGGAACA TGCTCAAGGT GATGACNNGG
321  ATGCACCGTG TGGTGGTCAT CTTCAAGCTC CTGGTACAGC
361  AGTTCTCGGT TCTGGAAACA ATGACTGCCT TGGACTTCAA
401  TGACTTCAGA GAGTACCTGT CTCCAGCATC AGGCTTCCAG
441  AGTCTTCAGT TCCGGCTGCT AGAAAATAAG ATAGGTGTTC
481  TTCAGAGCTT GAGAGTCCCT TACAACAGGA AACACTATCG
521  TGATAACTTT GAAGGAGACT ACAATGAGCT GCTCCCCCCC
561  CCCCC
```

FIG. 6

```
  1  ACCTCCGTGC TTCTCAGACA GTGCCTTTTC ACCATGAGTG
              Rat TO cDNA   AAC AGGGTAGGAT AT CTTTGAA
 41  GGTGCCCATT TTTAGGAAAC AACTTTGGAT ATACTTTTAA
      AAACTTATCT ATGGAAGACA ATGAAGAAGA CGGAGCTCAA
 81  AAAACTCCCC GTAGAAGGCA GTGAAGAAGA CAAATCACAA
      ACTGGTGTAA ACAGAGCCAG CAAAGGAGGA CTTATCTATG
121  ACTGGTGTGA ATAGAGCCAG CAAAGGAGGT CTTATTTATG
      GGGACTACTT GCAGTTGGAG AAGATTTTGA ATGCACAAGA
161  GGAACTACCT GCATTTGGAA AAAGTTTTGA ATGCACAAGA
      ACTTCAAAGT GAAATCAAAGGG AATAAAATC CACGACGAGC
201  ACTGCAAAGT GAA  CAAAAGGAAATAAAATC CATGATGAAC
      ACCTCTTTATTATAACTCACC AAG CTTATG AATCTTGGTT
241  ATCTTTTTTC ATAACTCATC AAGGCTTATG AA CTCTGGTT
      TAAACAAATT CTCTGGGAACTTTGATTCTGT TCGTGAGATT
281  TAAGCAAATC CTCTGGGAGT TGGATTCTGT TCGAGAGATC
      TTTCAAAATG GCCAATGTCAG GGATGAGAGG AACATGCTCA
321  TTTCAGAATG GCCA TGTCAG AGATGAAAGG AACATGCTTA
      AGGTGATGAC TCGGATGCAC CGTGTGGTGG TCATCTTCAA
361  AGGTTGTTTC TCGGATGCAC CGAGTGTCAG TGATCCTGAA
      GCTCCTGGTA CAGCAGTTCT CGGTTCTGGA AACAATGACT
401  ACTGCTGGTG CAGCAGTTTT CCATTCTGGA GACGATGACA
      GCCTTGGACT TCAATGACTT CAGAGAGTAC CTGTCTCCAG
441  GCCTTGGACT TCAATGACTT CAGAGAGTAC TTATCTCCAG
      CATCAGGCTT CCAGAGTCTT CAGTTCCGGC TGCTAGAAAA
481  CATCAGGCTT CCAGAGTTTG CAATTCCGAC TATTAGAAAA
      TAAGATAGGT GTTCTTCAGA GCTTGAGAGT CCCTTACAAC
521  CAAGATAGGT GTTCTTCAGA ACATGAGAGT CCCTTATAAC
      AGGAAACACT ATCGTGATAA CTTTGAAGGA GACTACAATG
561  AGAAGACATT ATCGTGATAA CTTCAAAGGA GAAGAAAATG
      AGCTGCTCC  Rat TO cDNA 551
601  AACTGCTACT TAAATCTGAG GCAGGAAAAG ACACTTCTGG
641  AATTAGTGGA GGCATGGCTG GAAAGAACTC CAGGTTTAGA
681  GCCACATGGA TTTAACTTCT GGGGAAAGCT TGAAAAAAAT
721  ATCACCAGAG GCCTGGAAGA GGAATTC
```

FIG. 7

```
-1652 AGGAAACTTTCTCAGCTCCAAAGGCCTAAAGAGAGTGGGATAAAATTAATTA -1601
     GCATAATCTCTGTAAACACGTACCCAGTTGAGCCACTATGTAGAGAAAGAGGGGCTGTTA -1561
                                         GRE -1515
     ACTGTTCTCTGCTGCCCAAACACTCTAAGCCAGGACACCAGGAAAAGCAACAGTGACTCC -1501
     ACCGCTCTCTCAGGTAAGGTCCCTATCCAGTGTGTAGGCAATTTCCAGGATCATTCATAA -1461
     AAACTCAAGGGAAATGTGACAGGTATAGCATATAGTTTTGATGATTTTCAAGTTCAATTA -1401
     TAACATGGCATTTGCATGTTGTTTATCTTTCTGTACTAGATATATAATTTATTATTCAGT -1361
             Insert
     AATA|AATCCAAGATTTTAACCTGGGTCAGGATCTTGAAGATTATAATCAGCTTAAACACT -1301
     TCCTATTTTGGTGAGGGAATTGATATGTACAGAAATTCAGTCAGTTTTTCTCATATTACA -1261
     AGGTAGTCGTAGAGCCAAGACTAGAAATCAGGTTTCTGACTTCCAATGACTTTGGCTAAT -1201
     TAGACACAATTCCATCATGGTAGATGATTAAATAAAGGCTAAGTGCTGTTTCTGCCTGTA -1161
     GTTCTTAGTGAGTAGCAGTGGCATGCTAAGGATAAGGCCATGAAGCTTCTATCCTGGCTT -1101
     AATTGTTCTCGGGGCAATTGTTTAGAGCTTAGATTAATAAATGATGTTTATGAAGCTTCT -1061
     ATCCTGGCTTAATTGTTCTCGGGGCAATTGTTTAGAGCTTAGATTAATAAATGATGTTTT  -901
     CAAGGAAGAATATTTTTATCACTGACACTGTATAGAATTATGGGCACATGGCTATTATTG  -861
 -860 GTT GTT GTT GTT GTT GTT GTT GTT GTT GTT repeat -823
     GTTCTTGTTGTTGTTGTTGTTGTTGTGTGTTTGTTTTGAGACAAAGTCTCACTCTGT  -801
     TGCCCAAGCTGGAGTGCCATGGCACAATCTT44GGCTCACTGCAACCTCCACCTCCTGGG  -741
     TTCAAGCGAGTCTCCTGCCTCAGCCTCCCTAGTAGCTGGGACTACAGGCACGCACCACCT  -681
     TGCCTGGCTAATGTTTTTGTAGTTTTAGTAGAGATAGAGTTTCGCTACGTTGGCCAGGCT  -621
     GGTCTTGAACTACTGTTTTAAAATTCTATATAGGCAATGTATGCTAATGTGGATGACTGC  -561
     TAGCTACCCTGTCATTGGTATGCCACAGATGAATAGTAAACTGATAATGTTCATTTAAAT  -501
     TCCAATACAATGTGTTGAGAGCTTAACTGCTGCTGATTATTACATGATATTTAGGTCAGA  -441
     AGAACTCTGATGATTGAATGGAAGTGGGCTTTGAGCATGTACCCAGACTTTATTATACAG  -401
     TTAATTTCCCTAGAGGTGTTAAATTTCAGTTTTTGGTCTAGAAGCTGTAAGAATAGTCAA  -341
     ATTTGAGAGAATACATATTTGTTTTTTACAAGCTCATCATCTTATGTATCCTAATACTAT  -301
             Insert -293
     TCCCACAT|GTTTTCTTGGGGAGGTGAATAAATGTAATTTTTTTAACTTGCCTCTGTTGAT  -241
                        -213
     TCATTGGATGTTTGTT\ACTTTGAATATAAAAGCAGAACTTGGCAAGTCATACAACTCAAT  -181
     TTGGCAGATCACTCACTCTTAGCACATGAACTGTGCCCAACATAAATCCACTCTAAAGTT  -121
                                                         -74
     TACAAGGGTGTCAGTTCTGTACCAATGGAAATGAGAAGTTAGCTAAGAGTAACAAGAAGC   -61
                               TATAA -24
     ATGCTGATTGCTGATGCAGGGTAAGCAGGCTACATAAAAGGCAGCTGTAGAACATCTGGG    -1
```

FIG. 8-1

```
+1  AAGGTCAATGATAGCATCTGCCTAGAGTCAAACCTCCGTGCTTCTCAGACAGTGCCTTTTCACC   64
                                     1
    ATG AGT GGG TGC CCA TTT TTA GGA AAC AAC TTT GGA TAT ACT TTT      109
    Met Ser Gly Cys Pro Phe Leu Gly Asn Asn Phe Gly Tyr Thr Phe       15

AAA AAA CTC CCC GTA GAA GGC AGC GAA GAA GAC AAA TCA CAA ACT      154
    Lys Lys Leu Pro Val Glu Gly Ser Glu Glu Asp Lys Ser Gln Thr       30

GGT GTG AAT AGA GCC AGC AAA GGA GGT CTT ATC TAT GGG AAC TAC      199
    Gly Val Asn Arg Ala Ser Lys Gly Gly Leu Ile Tyr Gly Asn Tyr       45
           2
    CTG CAT TTG GAA AAA GTT TTG AAT GCA CAA GAA CTG CAA AGT GAA      244
    Leu His Leu Glu Lys Val Leu Asn Ala Gln Glu Leu Gln Ser Glu       60

ACA AAA GGA AAT AAA ATC CAT GAT GAA CAT CTT TTT ATC ATA ACT      289
    Thr Lys Gly Asn Lys Ile His Asp Glu His Leu Phe Ile Ile Thr       75
            3
    CAT CAA GCT TAT GAA CTC TGG TTT AAG CAA ATC CTC TGG GAG TTG      334
    His Gln Ala Tyr Glu Leu Trp Phe Lys Gln Ile Leu Trp Glu Leu       90
                                           4
    GAT TCT GTT CGA GAG ATC TTT CAG AAT GGC CAT GTC AGA GAT GAA      379
    Asp Ser Val Arg Glu Ile Phe Gln Asn Gly His Val Arg Asp Glu      105

AGG AAC ATG CTT AAG GTT GTT TCT CGG ATG CAC CGA GTG TCA GTG      424
    Arg Asn Met Leu Lys Val Val Ser Arg Met His Arg Val Ser Val      120

ATC CTG AAA CTG CTG GTG CAG CAG TTT TCC ATT CTG GAG ACG ATG      469
    Ile Leu Lys Leu Leu Val Gln Gln Phe Ser Ile Leu Glu Thr Met      135
                                    5
    ACA GCC TTG GAC TTC AAT GAC TTC AGA GAG TAC TTA TCT CCA GCA      514
    Thr Ala Leu Asp Phe Asn Asp Phe Arg Glu Tyr Leu Ser Pro Ala      150

TCA GGC TTC CAG AGT TTG CAA TTC CGA CTA TTA GAA AAC AAG ATA      559
    Ser Gly Phe Gln Ser Leu Gln Phe Arg Leu Leu Glu Asn Lys Ile      165
                     6
    GGT GTT CTT CAG AAC ATG AGA GTC CCT TAT AAC AGA AGA CAT TAT      604
    Gly Val Leu Gln Asn Met Arg Val Pro Tyr Asn Arg Arg His Tyr      180

CGT GAT AAC TTC AAA GGA GAA GAA AAT GAA CTG CTA CTT AAA TCT      649
    Arg Asp Asn Phe Lys Gly Glu Glu Asn Glu Leu Leu Leu Lys Ser      195
                                            7
    GAG CAG GAA AAG ACA CTT CTG GAA TTA GTG GAG GCA TGG CTG GAA      694
    Glu Gln Glu Lys Thr Leu Leu Glu Leu Val Glu Ala Trp Leu Glu      210

AGA ACT CCA GGT TTA GAG CCA CAT GGA TTT AAC TTC TGG GGA AAG      739
    Arg Thr Pro Gly Leu Glu Pro His Gly Phe Asn Phe Trp Gly Lys      225

CTT GAA AAA AAT ATC ACC AGA GGC CTG GAA GAG GAA TTC ATA AGG      784
    Leu Glu Lys Asn Ile Thr Arg Gly Leu Glu Glu Glu Phe Ile Arg      240

ATT CAG GCT AAA GAA GAG TCT GAA GAA AAA GAG GAA CAG GTG GCT      829
    Ile Gln Ala Lys Glu Glu Ser Glu Glu Lys Glu Glu Gln Val Ala      255

GAA TTT CAG AAG CAA AAA GAG GTG CTA CTG TCC TTA TTT GAT GAG      874
    Glu Phe Gln Lys Gln Lys Glu Val Leu Leu Ser Leu Phe Asp Glu      270

AAA CGT CAT GAA CAT CTC CTT AGT AAA GGT GAA AGA CGG CTG TCA      919
    Lys Arg His Glu His Leu Leu Ser Lys Gly Glu Arg Arg Leu Ser      285
                                                         8
    TAC AGA GCA CTT CAG GGA GCA TTG ATG ATA TAT TTT TAC AGGGAA       964
    Tyr Arg Ala Leu Gln Gly Ala Leu Met Ile Tyr Phe Tyr Arg Glu      300
```

FIG. 8-2

```
GAG CCT AGG TTC CAG GTG CCT TTT CAG TTG CTG ACT TCT CTT ATG    1009
Glu Pro Arg Phe Gln Val Pro Phe Gln Leu Leu Thr Ser Leu Met     315
                                         9
GAC ATA GAT TCA CTG ATG ACC AAA TGG AGA TAT AAC CAT GTG TGC    1054
Asp Ile Asp Ser Leu Met Thr Lys Trp Arg Tyr Asn His Val Cys     330

ATG GTG CAC AGA ATG CTG GGC AGC AAA GCT GGC ACC GGT GGT TCC    1099
Met Val His Arg Met Leu Gly Ser Lys Ala Gly Thr Gly Gly Ser     345

TCA GGC TAT CAC TAC CTG CGT ACA CAT GTG AGT GAT AGG TAC AAG    1144
Ser Gly Tyr His Tyr Leu Arg Thr His Val Ser Asp Arg Tyr Lys     360

GTA TTT GTA GAT TTA TTT AAT CTT TCA CCA TAC CTG ATT CCC CGA    1189
Val Phe Val Asp Leu Phe Asn Leu Ser Pro Tyr Leu Ile Pro Arg     375

CAC TGG ATA CCG AAG ATG AAC CCA ACC ATT CAC AAA TTT CTA TAT    1234
His Trp Ile Pro Lys Met Asn Pro Thr Ile His Lys Phe Leu Tyr     390

ACA GCA GAA TAC TGT GAT AGC TCC TAC TTC AGC AGT GAT GAA TCA    1279
Thr Ala Glu Tyr Cys Asp Ser Ser Tyr Phe Ser Ser Asp Glu Ser     405

GAT TAA AATCGTCTGCAAAATCTATGAAGAATACTGGTTTCACAGCCTATTTTTATT    1337
Asp ***                                                         407

TTCTATGGATTTTCATAAATACAGTTTGAATATATGTATGCATATATTGTTCAGCACCAC   1397

GATGCTCTGATTTAATTCTAGAAACAATTTGATTACCTCTTGTTTGTGACAAGACTAAGC   1457

ATTAAGATGAGAAAGAATACATTTAAATAGTAACATTGTACATAGGGTGTTTTCCTATTA   1517
                                                        10
AAAATCAGTTTCCCCTGAGACTTAATGTAACCACTTAATGTAATCACTATCTCATTGTTT   1577

CATCTTTATAAACTTGTAAACTTCATCTATTTCAAATATTTTATGCAGTACATTATATTA   1637

TTCTGTACAAAGGCTTTCAAACAAAATTTTTAAAATAATAAAGTATTAATCTTTCAAAAA   1697

AAAAAAAAAAAAAAAA*                                              1714
```

AG - in bold represent the two sites where
     mutation causes hyperinduction of
     the TDO2 gene
Insert-indicates site of insert compared to rat sequence
GRE - glucocorticoind response elements
10 - numbers indicate sites of introns

FIG. 8-3

```
MSGCPFLGNNFGYTFKKLPVEGSEEDKSQTGVNRASKGGLIYGNYLHLEKVLNAQELQSE  60
::::::  ::   :::  :::: :::::::::::::::: : : ::: :::::::::
MSGCPFSGNSVGYTLKNLSMEDNEEDGAQTGVNRASKGGLIYGDYLQLEKILNAQELQSE  60

TKGNKIHDEHLFIITHQAYELWFKQILWELDSVREIFQNGHVRDERNMLKVVSRMHRVSV 120
:::::::::::::::::::::::::::::::::::::::::::::::::: :::::::
IKGNKIHDEHLFIITHQAYELWFKQILWELDSVREIFQNGHVRDERNMLKVMTRMHRVVV 120

ILKLLVQQFSILETMTALDFNDFREYLSPASGFQSLQFRLLENKIGVLQNMRVPYNRRHY 180
::::::::::: :::::::::::::::::::::::::::::::::::   :::::: ::
IFKLLVQQFSVLQTMTALDFNDFREYLSPASGFQSLQFRLLENKIGVLQSLRVPYNRKHY 180

RDNFKGEENELLLKSEQEKTLLELVEAWLERTPGLEPHGFNFWGKLEKNITRGLEEEFIR 240
:::: :  ::::::::::: :::::::::::::::::::::::::::::::::::::::
RDNFEGDYNELLLKSEQEQTLLQLLEAWLERTPGLEPHGFNFWGKFEKNILKGLEEEFLK 240

IQAKEESEEKEEQVAEFQKQKEVLLSLFDEKRHEHLLSKGERRLSYRALQGALMIYFYRE 300
:::::::::::: ::::::::::::::::::::::::::::::::::::::::::
IQAKKDSEEKEEQMAEFRKQKEVLLCLFDEKRHDYLLSKGERRLSYRALQGALMIYFYRE 300

EPRFQVPFQLLTSLMDIDSLMTKWRYNHVCMVHRMLGSKAGTGGSSGYHYLRTHVSDRYK 360
::::::::::::::::::::::::::::::::::::::::::::: :::: ::::::
EPRFQVPFQLLTSLMDIDTLMTKWRYNHVCMVHRMLGSKAGTGGSSGYYYLRSTVSDRYK 360

VFVDLFNLSPYLIPRHWIPKMNPTIHKFLYTAEYCDSSYFSSDESDO             407
::::::::: ::::::::::::::: :::::::::: :::::::::
VFVDLFNLSSYLVPRHWIPKMNPIIHKFLYTAEYSDSSYFSSDESDO             407
```

Aligned 407, Matches 357, Mismatches 50, Homology 87%

FIG. 10

```
                                      52
AGGAAACTTCTCAGCTCCAAAGGCCTAAAGA GAGTGGGATAAAATTAATTAGCATAATC
              51
TCTGTAAACAC GTACCCAGTTGAGCCACTATGTAGAGAAAGAGGGGCTGTTAACTGTTC
TCTGCTGCCCAAACACTCTAAGCCAGGACACCAGGAAAAGCAACAGTGACTCCACCGCTCT
CTCAGGTAAGGTCCCTATCCAGTGTGTAGGCAATTTCCAGGATCATTCATAAAAACTCAAG
GGAAATGTGACAGGTATAGCATATAGTTTTGATGATTTTCAAGTTCAATTATAACATGGCA
TTTGCATGTTGTTTATCTTTCTGTACTAGATATATAATTTATTATTCAGTAATGGAATCAA
                 47
GATTTTAACCTGGGTCA GGATCTTGAAGATTATAATCAG CTTAAACACTTCCTATTTTG
GTGAGGGAATTGATATGTACAGAAATTCAGTCAGTTTTTCTCATATTACAAGGTAGTCGTA
GAGCCAAGACTAGAAATCAGGTTTCTGACTTCCAATGACTTTGGCTAATTAGACACAATTC
CATCATGGTAGATGATTAAATAAAGGCTAAGTGCTGTTTCTGCCTGTAGTTCTTAGTGAGT
AGCAGTGGCATGCTAAGGATAAGGCCATGAAGCTTCTATCCTGGCTTAATTGTTCTCGGGG
CAATTGTTTAGAGCTTAGATTAATAAATGATGTTTCAAGGAAGAATATTTTTAT CACTCAC
        48
ACTGTATAGAATTATGG GCACATGGCTATTATTGGTTCTTGTTGTTGTTGTTGTTG
                                                   45
TTGTGTGTTTGTTTTGAGACAAAGTCTCACTCTGTTGCCCAAGCTG GAGTGCCATGGCA
       44
CAATCTT GGCTCACTGCAACCTCCACCTCCTGGGTTCAAGCGAGTCTCCTGCCTCAGCC
                              50
TCCCTAGTAGCTGGGACTACAGGCACG CACCACCTTGCCTGGCTAAT GTTTTTGTAGTT
TTAGTAGAGATAGAGTTTCGCTACGTTGGCCAGGCTGGTCTTGAACTACTGTTTTAAAATT
                                            42
CTATATAGGCAATGTATGCTAATGTGGATGACTGCTAGCTACCCTGTC ATTGGTATGCC
ACAGATG AATAGTAAACTGATAATGTTCATTTAAATTCCAATACAATGTGTTGAGAGCTTA
ACTGCTGCTGATTATTACATGATATTTAGGTCAGAAGAACTCTGATGATTGAATGGAAGTG
GGCTTTGAGCATGTACCCAGACTTTATTATACAGTTAATTTCCCTAGAGGTGTTAAATTTC
AGTTTTTGGTCTAGAAGCTGTAAGAATAGTCAAATTTGAGAGAATACATATTTGTTTTTA
CAAGCTCATCATCTTATGTATCCTAATACTATGCCACATGTTTTCTNGGGGAGGTGAATAA
            39                       38
ATGTAATTTTTTTA ACTTGCCTCTGTTGATTCAT TGGATGTTTGTTACTTTGAATAT
AAAAGCAGAACTTGGCAAGTCATACAACTCAATTTGGCAGATCACTCACTCTTAGCACATG
                                                       40
AGCTGTGCCCAACATAAATCCACTCTAAAGTTTACAGAGGTTCAGTTCTGT ACCAATGG
AAATGAGAAGTT AGCTAAGAGTACAAGAAGCATGCTGATTGNCTGATGCAGGGTAAGCAGG
CTACATAAAAGGCAGCTGTAGAACATCTGGG
(start of c-DNA Exon 1)
                                  43            14
AAGGTCAATGATAGCATCTGCCTAGAGTCAA. ACCTCCGTGCTTCT CAGA
     33           20
CAGTGCC TTTTCACCAT GAGTGGGTGCCCATTTTTAGGAAACAACTTTG
(Intron 1)
GGGTGAGTATTTACCTTTATTCTAAGTGGGTTTGGGCTTTTAGAAGTATCAGGTGTGAGCA
TTTTAATTTCTGAATTTAAGGAGCATTGAAAACTGTCACCTTTATNCCTTGGTCTAACANT
CTACTCTAAAGAAAATTNGCAATGAFAATTTTAATCACCCATATCATTAGTTAACTGTGTT
TTCTAAAGCACTATTTTCCCCTCTTGATTTATTAAATTNGCA
(Exon 2)
                         22
GATATACTTTTAAAAAACTCCCC GTAGAAGGCAGCGAAGAAGA CAAATCACA
AACTGGTGTGAATAGAGCCAGCAAAGGAGGTCTTATCTATGGGAACTACCTGCA
T
(Intron 2)
GTAAGTGGCAGGGTCCTTACAGGGTNTGGNGTCCATTGTTAGGCCACTCAATTCTGCCAAG
TGACTTCNNATGATCTCATTTCTNGGAATCA...
TACTAAAGNTGATAAAAACCAAGNNCTGCAATTTCAGACAGGCNTTTTATTTGNTCATTTC
AAG
(Exon 3, TGH-09 T7 inv)
TTGGAAAAAGTTTTGAATGCACAAGAACTGCAAAGTGAAACAAAAGGAAATAAA
ATCCATGATGAACATCTTTTTATCATAACTCATCAAG
```

FIG. 11-1

(Intron 3)
GTAAGTTGCACAAAGGTTTTGGACAATATTCCACAGGCATTTCTCATTGATAACGAGGAAA
GCTACAATTTTTAAACTACAAAATGATGAAAGATCATGGAATCACCTCTGTTAGAAATGTT
TGAGAATATTTTGCTGCCAGATG...
(Exon 4)
CTTATGAACTCTGGTTTAAGCAAATCCTCTGGGAGTTGGATTCTGTTCGAGAGA
TCTTTCAGAATGGCCAT...
(Intron 4)
ATTGCATTGTTATTGTATTTCTAAGAGGTCAGCATTGCTAACGCAGTGTTTCATTTCTTAA
CCTTAG
(Exon 5, TGH-07 T3)
GTCAGAGATGAAAGGAACATGCTTAAGGTTGTTTCT~~CCCATGGAGGGAGTGTCA~~
  25                                                        27
GT  GATCCTGAAACTGCTGGTGCAGCAGTT~~TTCCATTCTGGAGACGAT~~  GAC
AGCCTTGGACTTCAATGACTTCAG
(Intron 5)
GTGTGCACATTTGGCATTTTAAAAATGTGATGGAATTTACTTTCTCATTTTGGT
GGGTAAAGTACTCATGTGTGTGTGTGCATGAGGAGCCTGTCTTACTAACATTGT
CACACATAATGGACTTAGGGCCTCGATCACAAGCATTGAGAGTTATTAAATATT
ATATCATTACCATGTAGCGTATATG...
(Exon 6)
AGAGTACTTATCTCCAGCATCAGGCTTCCAGAGTTTGCAATTCCGACTATTAGA
AAACAAGATAGGTGTTCTTCAGAAC...
(Intron 6)
TCTTCATGCAAG
(Exon 7, TGH-07 T7 inv)
 26
A  ~~TGAGAGTCCCTTATAACAGA~~AGACATTATCGTGATAACTTCAAAGGAGAAG
AAAATGAACTGCTACTTAAATCTGAGCAGGAAAAGACACTTCTGGAATTAGTGG
AG
(Intron 7)
GTATGGATTCATACAATTTATAAAGTTTAACTCAATACATCTTCTTAATTTAGC
TTTTGCTAAATCAGAATTTTAAAAAACGTATATCGAAACTGAGTTACATTCAGTG
GAAATAAGGATA...
(Exon 8)
GCATGGCTGGAAAGAACTCCAGGTTTAGAGCCACATGGATTTAACTTCTGGGGA
AAGCTTGAAAAAAATATCACCAGAGGCCTGGAAGAGGAATTC
(joint of HT03)
ATAAGGATTCAGGCTAAAGAAGAGTCTGAAGAAAAAGAGGAACAGGTGGCTGAA
TTTCAGAAGCAAAAAGAGGTGCTACTGTCCTTATTTGATGAGAAACGTCATGAA
CATCTCCTTAGTAAAGGTGAAAGACGGCTGTCATACAGAGCACTTCAGGGAGCA
TTGATGATATATTTTTACAG...
(Tent intron 8)
CCAACTGATTGTCAAACTCATGCTCCTCCAACACATCGATTTAVTTGAATATATTCTTCTT
TTTCTTCTTTTTTTCCTTTAG
(Tent.Exon 9, TGH-03 SK)
GGAAGAGCCTAGGTTCCAGGTGCCTTTTCAGTTGCTGACTTCTCTTATGGACAT
AGATTCACTGATGACCAAATGGAGAT
(Tent intron 9)
GTAGTCCTCCCACTCACCCATGTTGCTTCCCACATGCGTTCTGTCTCTTATCTT..
(Tent Exon 10)
ATAACCATGTGTGCATGGTGCACAGAATGCTGGGCAGCAAAGCTGGCACCGGTG
                                                   37
GTTCCTCAGGCTATCACTACCTGCGTACACATG~~TGAGTGATAGGTACAAGG~~  T
ATTTGTAGATTTATTTAATCTTTCACCATACCTGATTCCCCGACACTGGATACC
GAAGATGAACCCAACCATTCACAAATTTCTATATACAGCAGAATACTGTGATAG
.CTCCTACTTCAGCAGTGATGAATCAGATTAAAATCGTCTGCAAAATCTATGAA
GAATACTGGTTTCACAGCCTATTTTTTATTTTCTATGGATTTTCATAAATACAG
TTTGAATATATGTATGCATATATTGTTCAGCACCACGATGCTCTGATTTAATTC
TAGAAACAATTTGATTACCTCTTGTTTGTGACAAGACTAAGCATTAAGATGAGAAAGAAT
ACATTTAAATAGTAACATTGTACATAGGGTGTTTTCCTATTAAAAATCAGTTTCCCCTGAG

FIG. 11-2

ACTTAATGTAACCACTTAATGTAATCACTATCTCATT
(Tent Exon 11)
GTTTCATCTTTATAAACTTGTAAACTTCATCTATTTCAAATATTTTATGCAGTA
CATTATATTATTCTGTACAAAGGCTTTCAAACAAAATTTTTAAAATAATAAAGT
ATTAATCTTTC
(end of gene)
TCCCTGTATTGTTTTTGAAATATTGATTGTATTTGTTAGGAATCTTAATGACCAAAGACAG
AAATCTATCTGAAGTTTGTCTAGAGGGNATATACTGAAGAATTACTAGCTT...
AAAAAAAAAAAAAAAAAAAAA*

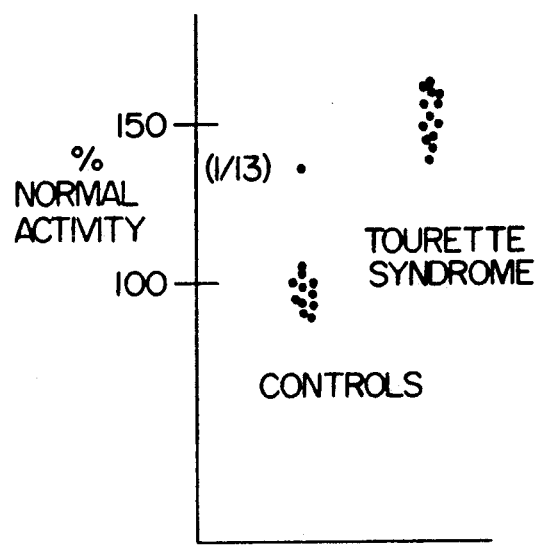
FIG. 14
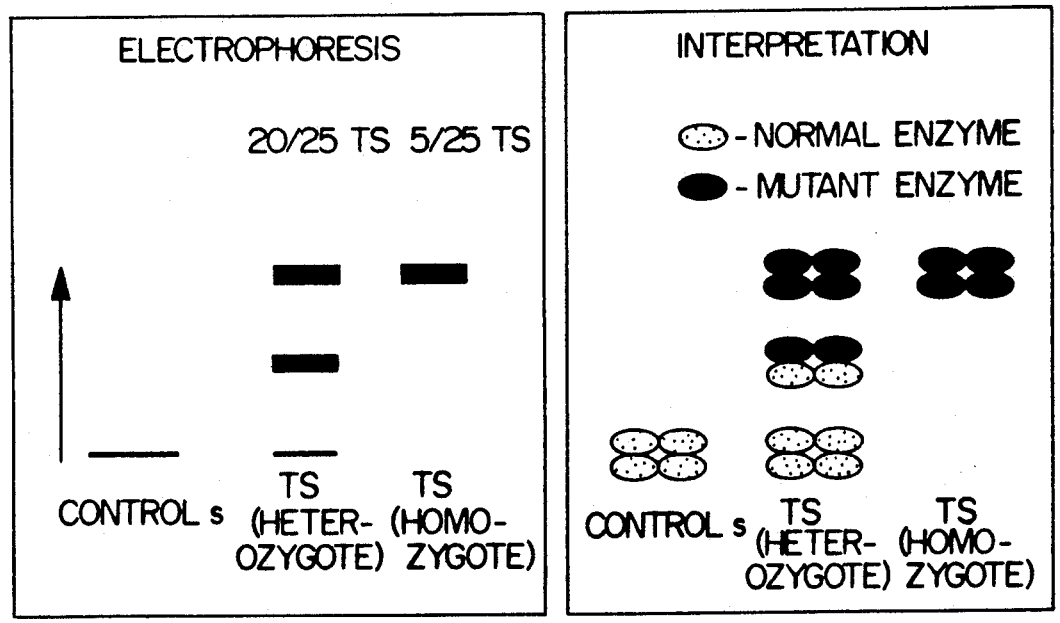
FIG. 15A
FIG. 15B

METHOD FOR THE DIAGNOSIS OF TOURETTE SYNDROME AND ASSOCIATED DISORDERS

This application is a continuation-in-part of each of copending application Ser. No. 125,577 (now abandoned) filed Nov. 25, 1987, copending application Ser. No. 271,653 filed Nov. 16, 1988, copending application Ser. No. 410,831 (now abandoned) filed Sep. 22, 1989, and copending application Ser. No. 562,596 filed Aug. 3, 1990.

Each of these copending applications is incorporated into this application by reference.

BACKGROUND

Tourette syndrome (TS) is a common, hereditary, neurobehavioral disorder characterized by motor and vocal tics. In addition to the tics the applicant has shown that TS is associated with a wide range of other behavioral disorders in both the patients and their relatives. These include attention deficit disorder (ADD) with or without hyperactivity, autism (a trait of three sets of symptoms: (1) a profound failure to develop social relationships; (2) defective speech and language; and (3) ritualistic or compulsive behavior), obsessive-compulsive behaviors, unipolar or bipolar affective disorder, phobias, panic attacks, premenstrual syndrome (PMS), generalized anxiety disorder, pervasive developmental disorder, dyslexia, learning disabilities, dysgraphia, mental retardation, specific math disabilities, specific reading disabilities, specific spelling disabilities, borderline personality disorder, migraine headaches, exhibitionism, stuttering, delayed speech, schizophreniform disorder, schizoid disorder, drug or alcohol addiction or abuse, bulimia, compulsive eating with obesity, physical or sexual abuse of spouse or children, somatiform disorders including spastic colon, (irritable bowel syndrome), chronic fatigue syndrome, sleep disturbances, sleep apnea, sudden infant death syndrome (SIDS), narcolepsy, insomnia, short temper, and temper tantrums.

Hereinafter these abnormalities are collectively referenced as "TS related disorders" or "TS spectrum of disorders."

The applicant has proposed that the symptoms of TS, and TS related disorders, fit a model in which the frontal lobe and limbic system in the brain are disinhibited by a relative deficiency in brain serotonin and tryptophan and that these chemical deficiencies are due to genetic defects in the two major genes that cause the breakdown of tryptophan—tryptophan 2,3-dioxygenase and indoleamine 2,3- dioxygenase and that tests for mutations in these genes will be an extremely useful adjunct in the diagnosis and treatment of TS and TS associated behaviors.

Tryptophan 2,3-dioxygenase (tryptophan oxygenase, tryptophan pyrrolase) and indoleamine 2,3 dioxygenase, are similar but separate enzymes. See Gal, E. M. and Sherman, A. D., "DL-kynurenine: its synthesis and possible regulatory function in brain", Neurochem.Res. 5:223-239 (1980).

Table 1 depicts several apparent similarities and differences between the functions of these enzymes. See Hayaishi, O., "Properties and function of indoleamine 2,3-dioxygenase," Biochem. 79:13p-21p (1976); Gal, E. M., "Cerebral tryptophan-2,3-dioxygenase (pyrrolase) and its induction in rat brain" Neurochem. 22:861-863 (1974); and Gal, E. M. and Sherman, A. D. "DL-kynurenine: its synthesis and possible regulatory function in brain", Neurochem. Res. 5:223-239 (1980).

TABLE 1

| | Tryptophan 2,3-dioxygenase | Indoleamine 2,3-dioxygenase |
|---|---|---|
| Similarities | | |
| Substrate | L-tryptophan | L-tryptophan |
| Oxygen | Oxygen | |
| Product | N-formyl L-kynurenine | N-formyl L-kynurenine |
| Cofactor | heme | heme |
| Induced by: | tryptophan | tryptophan |
| Differences | | |
| Location | liver, red blood cells, brain | intestine, brain other organs |
| Type of oxygen used | $O_2$ | $O-O^-$ |
| Other substrates | none | D-tryptophan 5-hydroxy-tryptophan serotonin melantoin |
| Inducible by steroids | yes | no |
| Inducible by interferon | no | yes |

The nucleotide sequence of human indoleamine 2,3-dioxygenase has been published. See Gupta S. L. and Dal, W. "Molecular cloning, sequencing and expression of human interferon-gamma-inducible indoleamine 2.3-dioxygenase cDNA" Biochem. Biophys. Res. Comm. 168:1-8 (1990). Comparison of this published sequence of indoleamine 2,3-dioxygenase with the sequence of tryptophan dioxygenase disclosed (See FIG. 8) indicates that the two enzymes are produced by different genes. Accordingly, the predominantly liver enzyme, tryptophan 2,3-dioxygenase is referred to herein as TD02, the brain-intestine enzyme, indoleamine 2,3-dioxygenase is referred to as ID02. Collectively, these two enzymes are labelled TD02-ID02 which means TD02 and/or ID02.

If TD02-ID02 activity were present only in the liver-intestine, then the level of tryptophan in the brain would be almost completely dependent on the blood level of tryptophan and of the other large amino acids that compete for its transport across the blood brain barrier. However, as FIG. 1 shows, TOD2-ID02 activity is present in the brain where it is effective to siphon off some of the tryptophan after entry into the brain and before it is converted to serotonin. In rats, under normal conditions 70% of the brain tryptophan is converted to serotonin and 30% to brain kynurenine. See Gal, E. M. and Sherman, A. D., "DL-kynurenine: its synthesis and possible regulatory function in brain", Neurochem. Res. 5:223-239 (1980).

Thus, even a moderate increase in brain TD02-ID02 activity could markedly change this ratio and lower the level of brain serotonin. Significant changes in the breakdown of tryptophan in the brain may thus occur concurrently with only moderate changes in the blood tryptophan and serotonin.

In humans, serotonin and tryptophan levels are apparently interdependent, serotonin level abnormalities being a consequence of tryptophan level abnormalities. As FIG. 2 shows, peripheral tryptophan can take two major metabolic pathways, i.e., 90% conversion to kynurenine and 10% conversion to serotonin. TD02-ID02 activity is the rate limiting step in the degradation of tryptophan to kynurenine.

Mutations of the TD02-ID02 genes are implicated in TS and TS associated behaviors and changes in the level of these enzymes would be expected to significantly affect serotonin production. While it is anticipated that TS and most of the TS related disorders will be due to mutations that increase the level of TD02-ID02, since some TS or autistic children have either too low or too high levels of serotonin, the basic defect is both may be a "dysregulation" of serotonin usually a result of too much, but occasionally too little, TD02-ID02.

FIG. 3 indicates that genetic defects in TD02-ID02 that may occur in TS, and TS related disorders, and in autism. The applicant's studies show that children with autism often develop full blown symptoms of TS as they grow older. (See Comings, D. E. and Comings, B. G., "Clinical and genetic relationships between autism-PDD and Tourette syndrome: A study of 19 cases." *Amer. J. Med. Genetics* 39:180–191 (1991). Thus many cases of autism may in fact be due to the same genetic defect that causes TS.

SUMMARY OF THE INVENTION

This invention includes any test that assays or determines the functional integrity of tryptophan oxygenase (tryptophan 2,3-dioxygenase, TD02 or indoleamine 2,3-dioxygenase, ID02) in relationship to Tourette syndrome and TS associated behaviors, or TS spectrum disorders, whether that test is to determine changes in the nucleotide sequence of any part of the gene, the expression of TD02-ID02 messenger RNA, the expression or activity of the TD02-ID02 protein or enzyme, or electrophoretic variants of the TD02-ID02 protein or enzyme in any tissue or bodily fluid.

Diagnostic tests are provided for, among other things, Tourette syndrome (TS), and TS associated behaviors including chronic motor and vocal tics, attention deficit disorder (ADD) with or without hyperactivity, autism, obsessive-compulsive behaviors, depression or mania (unipolar or bipolar affective disorder) disorder, phobias, panic attacks, premenstrual syndrome (PMS), generalized anxiety disorder, pervasive developmental disorder, dyslexia, learning disabilities, mental retardation, dysgraphia, specific math disabilities, specific reading disabilities, specific spelling disabilities, borderline personality disorder, migraine headaches, exhibitionism, stuttering, delayed speech, schizophreniform disorder, schizoid disorder, drug or alcohol addiction or abuse, bulimia, compulsive eating with obesity, physical or sexual abuse of spouse or children, somatiform disorders including spastic colon, (irritable bowel syndrome), chronic fatigue syndrome, sleep disturbances, sleep apnea, sudden infant death syndrome (SIDS), narcolepsy, insomnia, short temper, and temper tantrums.

All of these disorders have been noted to be present in TS patients and their relatives at a greater frequency than in the general population. All of these different disorders are controlled by the limbic system, frontal lobes and hypothalamus, which in turn are dependent upon a normal level of brain serotonin to function properly. When serotonin metabolism is defective, due to a mutation affecting the level of the enzyme tryptophan oxygenase, any or all of these disorders may occur.

The fact that TS is a wide-based, generalized behavioral disorder associated with the above list of abnormalities is documented in Comings, D. E. and Comings, B. G., "A controlled study of Tourette syndrome. I. Attention deficient disorder, learning disorders and school problems" *Amer. J. Human Genetics* 41:701–741 (1987); Comings, D. E. and Comings, B. G., "A controlled study of Tourette syndrome. II. Conduct disorder" *Amer. J. Human Genetics* 41:742–760 (1987); Comings, D. E. and Comings, B. G., "A controlled study of Tourette syndrome. III. Phobias and panic attacks" *Amer. J. Human Genetics* 41:761–781 (1987); Comings, D. E. and Comings, B. G., "A controlled study of Tourette syndrome. IV. Obsessive compulsive and schizoid behavior" *Amer. J. Human Genetics* 41:782–803 (1987); Comings, D. E. and Comings, B. G., "A controlled study of Tourette syndrome. V. Depression and mania" *Amer. J. Human Genetics* 41:804–821 (1987); Comings, D. E. and Comings, B. G., "A controlled study of Tourette syndrome. VI. Early development, sleep problems, allergies and handedness" *Amer. J. Human Genetics* 41:822–838 (1987); Comings, D. E. and Comings, B. G., "A controlled family history study of Tourette syndrome, I. Attention deficit hyperactivity disorder, learning disorders and dyslexia" *J. Clin. Psychiatry* 51:275–280, (1990); Comings, D. E. and Comings, B. G., "A controlled family history study of Tourette syndrome, II. Alcoholism, drug abuse and obesity" *J. Clin. Psychiatry* 51:281–287 (1980); Comings, D. E. and Comings, B. G., "A controlled family history study of Tourette syndrome, III. Other psychiatric disorders" *J. Clin. Psychiatry* 51:288–291, (1990); Comings, D. E., Tourette Syndrome and Human Behavior, Hope Press, Duarte, CA 91009-0188, 830 pages (1990).

This invention covers techniques for the diagnosis of TS and TS related disorders utilizing testing of abnormalities in TD02-ID02. The diagnosis is accomplished by genetic tests to identify mutations in the TD02-ID02 genes which may cause such psychiatric, behavioral and physical disorders. To that end, the invention includes the identification, chromosomal location, nucleotide sequence and encoded peptide sequence of the human TD02 gene, and the demonstration that TD02 is mutated such that its level of activity is increased (or altered) in Tourette syndrome and TS related disorders.

It is anticipated that the mutations causing hyperinducability or increased activity of the TD02-ID02 genes occur in or near the promoter regions of the 5' regulatory sequences of the TD02-ID02 genes in or near glucocorticoid response elements (GRE) or other induction response elements, or in the expressed-translated portions of the gene, affecting heme, tryptophan, copper or 02 or O-binding at or near or the active catalytic site.

The diagnostic tests of the invention include detection of mutations or alterations of TD02-ID02 genes by any technique, including electrophoretic patterns of fragments produced by cutting portions of the TO or IO genes with restriction enzymes, including after amplification, e.g., by the polymerase chain reaction (PCR) or other related techniques, allele specific PCR, see Newton, C. R., et al., Analysis of any point mutation in DNA. The amplification refractory mutation system (ARMS), *Nucleic Acids Research* 17:2503–2516 (1989) and reverse allele specific testing, see Wallace, application Ser. No. 07/283,142, and its continuation-in-part, Ser. No. 07/678,448, or any other technique to detect changes in tbe nucleotide sequence of TD02-ID02, assay of TD02-ID02 activity in red blood cells, white blood cells or other cellular or fluid components, the electrophoresis of TD02-ID02 to show mutant forms of the enzymes, or testing for abnormalities in the sequence or amount of TD02-ID02 messenger RNA.

BRIEF DESCRIPTION OF THE FIGURES

FIGS. 5-1, 5-2, 5A-1, 5A-2 and 5A-3 depict the sequence of the human HT03 (TD02) clone and the translation into the open reading frame.

FIG. 6 depicts the sequence of rat pcTOI and rat TD02.

FIG. 7 shows the region of homology between the sequences depicted by FIGS. 5 and 5a and by FIG. 6.

FIGS. 8-1, 8-2 and 8-3 depicts the sequence of the entire expressed portion and regulatory sequences of the human TO gene (TD02).

FIG. 10 is a comparison of the amino acid sequenc of the rat (Maezono, K., et al., Deduced primary structure of rat tryptophan-2,3-dioxygenase, *Biochem. Biophys. Res. Comm.* 176-181 (1990)) versus the human tryptophan oxygenase gene.

FIGS. 11-1, 11-2 and 11-3 depicts the sequence of some of the TD02 introns.

FIG. 12 depicts the results of hybridization studies to identify the chromosomal location of the human TDO gene.

FIG. 14 depicts the results of an assay which compares the activity of tryptophan oxygenase in controls and in patients with TS.

FIG. 15A depicts the results of electrophoresis of the red blood cell lysate, in conjunction with assay in the gel, for TD02 activity of controls and TS patients.

FIG. 15B illustrates an interpretation of FIG. 15A.

DETAILED DESCRIPTION OF THE INVENTION

Figure 1:
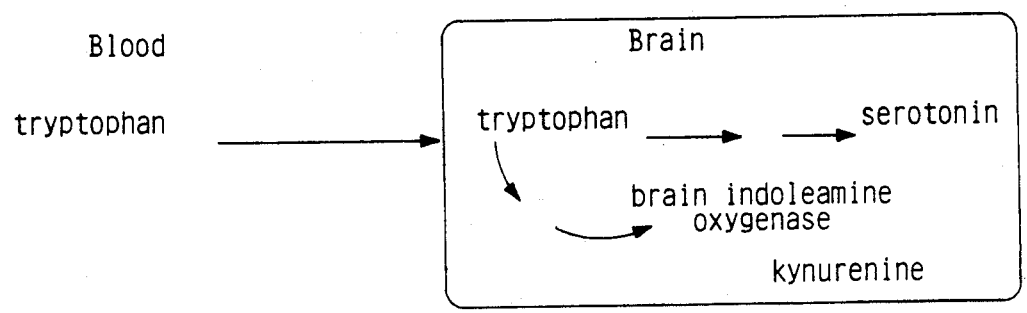
FIG. 1 is a schematic illustration of TD02-ID02 activity present in the brain.
Figure 2:
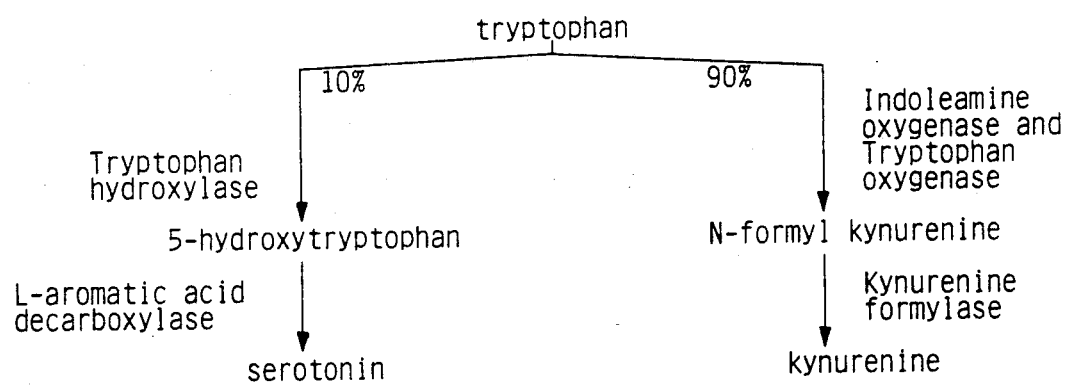
FIG. 2 is a schematic illustration of two metabolic pathways available to peripheral tryptophan.
Figure 3:
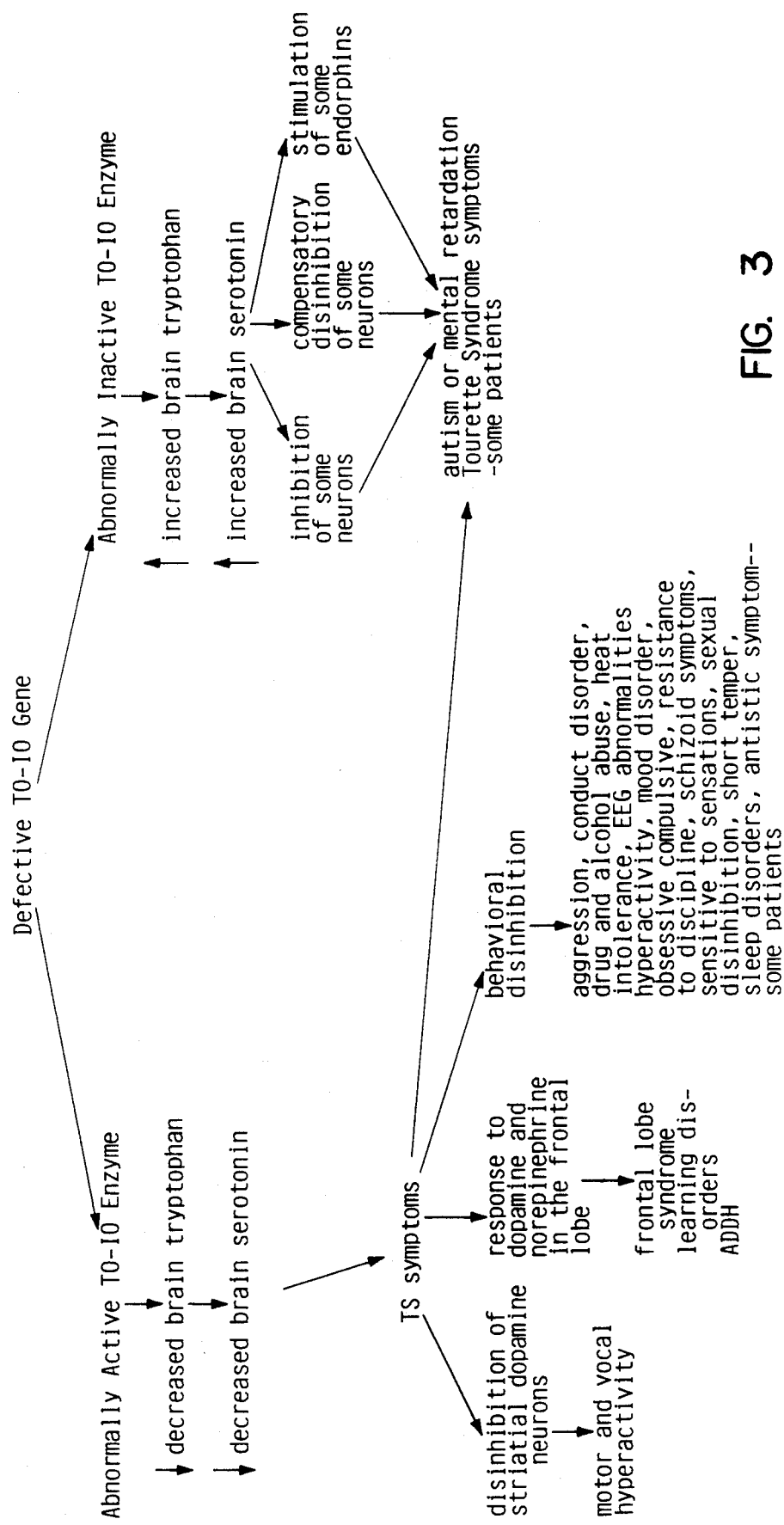
FIG. 3 indicates genetic defects in TD02-ID02 that may occur in TS, TS related disorders and autism.

This invention provides genetic tests for TS and TS related disorders listed in "Summary of the Invention". These tests entail the identification of deletions, duplications, nucleotide changes and other defective alleles of the TD02-ID02 gene(s). These genetic tests, per se, may be of conventional nature and involve, for example:

(a) Obtaining DNA from subjects to be tested (blood, skin, urine, buccal smear, hair follicles or any other source).

(b) Identifying mutations in this DNA by hybridization of specific DNA or RNA probes to various parts of the TD02-ID02 genes, or DNA surrounding the TD02-ID02 genes. The mutations may be partial or complete gene duplications, double or multiple gene duplications, partial or complete gene deletions, single or multiple nucleotide substitutions, insertions or deletions, or frame shift mutations. The probes may, for example, be oligonucleotide probes including allele specific synthetic oligonucleotides, cloned cDNA, genomic DNA fragments, or RNA. The test may include hybridization of DNA electrophoresed in gels, or spotted on a support media, or amplified by DNA polymerases. The invention includes cloned cDNA and genomic DNA probes for the human TD02-ID02 genes useful to conduct such genetic tests. The invention also includes an isolated or synthetic DNA sequence comprising at least a portion of the TD02-ID02 gene sequence, and isolated or synthetic proteins encoded by the TD02-ID02 gene sequence in whole or in part.

(c) Assays of TD02-ID02 enzyme activity in red blood cells, white blood cells, or other cells or bodily fluids, (d) Electrophoresis of TD02-ID02 enzymes in red blood cells, white blood cells, or other cells or bodily fluids.

CLONING OF THE HUMAN TO GENE

Schmidt, et al. report the isolation of the rat liver tryptophan oxygenase gene. See *EMBO Journal* 1:1287 (1982). Two cDNA probes, pcTOI and pcT02 covering parts of the entire rat TO gene are described. To provide an appropriate human cDNA probe, the rat pcTO 570 base pair clone was labelled with 32p and hybridized to a Clonetech human liver cDNA library (Clonetech Laboratories, Inc., Human Liver cDNA, Library Catalogue No. HL101B, Lot No. 2102).

The Clonetech cDNA library to human liver messenger RNA, in XGT11, was plated on LB plates at a density of 30,000 pfu, using LE392 host E. coli. Plaques were lifted in duplicate on BA85 circles, washed in 0.5N NaOH, 1.5M NaCl, then 0.5M Tris, pH 8, 1.5M NaCl, then baked 2 hours at 80° C. The filters were then prehybridized 2 hours in 6X SSC, 1X Denhardts, 100 ug/ml salmon sperm DNA at 65.C, 0.2 ml/sq.cm.

The 565 base pair pcT01 insert DNA was labelled with 32p by nick translation and hybridized overnight in 6X SSC, 1X Denhardts, 0.1% SDS, 65.C, then washed in 2X SSC, 1X Denhardts at room temperature for 30 min, then twice in 0.3X SSC, 0.5% SDS, 65° C. for 1 hour. Seventeen of the plaques that were positive on both duplicate plaque lifts were identified and replated at low density, about 100 plaques per disk, and final single plaques grown up of each positive clone.

Non-specific artifacts were ruled out if a positive signal (dark spot on the autoradiogram) was obtained in the same position on each duplicate lift as determined by superimposing the two autoradiograms in a slightly shifted position and examination for double spots.

Figure 4:
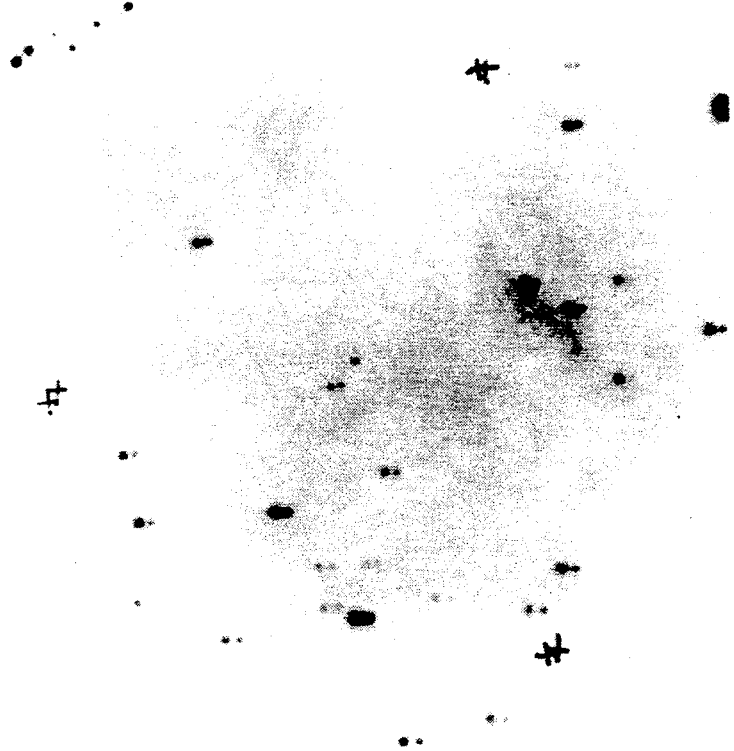
FIG. 4 depicts audioradiograms of duplicate filter lifts from a human liver cDNA library in gt 11 hybridized with rat liver superimposed and turned slightly to reveal human cDNA clones of human tryptophan oxygenase.

FIG. 4, from just one of nine different dishes, depicts autoradiograms of duplicate filter lifts superimposed and turned slightly. Double spots (duplicate hybridizations) each represent presumptive human cDNA clones of human tryptophan oxygenase. The +'s are orientation markers.

To ascertain if these presumptive clones truly represent human TO, the rat pcTOl cDNA and one of the human cDNA clones (HT03) were sequenced, using the Sanger method. The sequence of human HT03 (TD02) clone and the translation into protein to the open reading frame are shown in FIGS. 5-1, 5-2, 5A-1, 5A-2 and 5A-3, the sequence of the rat pcTOI and rat TD02 is shown in FIG. 6, and the region of homology between the two is shown in FIG. 7. The fact that all base pairs of the rat were 80% homologous with the human HT03 sequence and that the amino acid sequence of the human TD02 and the rat TD02 match were 88% homologous indicates that the human TD02 cDNA was isolated.

To sequence the regulatory region and some of the introns of the human TD02 gene required the isolation of genomic clones. Table 2 lists the cDNA and genomic clones used and the method of their isolation.

TABLE 2
Human TDO2 cDNA and Genomic Clones

| Clone | Source | Vector | Size (kb) | Probe |
|---|---|---|---|---|
| HT03 | Clontech HL10016 human liver cDNA | gt11 | 1.7 | Rat pCT01 |
| TGH-01 | Human Genomic Library[33] | Charon 4A | 20.0 | HTO3 |
| TGH-031 | Human Genomic Library[33] | Charon 4A | 1.7 | HTO3 |
| TGH-041 | Human Genomic Library | Charon 4A | 1.45 | HTO3 |
| TGH-07 | Chrom 4 Library LA04NS02 | EMBL 3 | 1.5 | HTO3 |
| TGH-09 | Chrom 4 Library LA04NS01 | EMBL 3 | 2.0 | HTO13.12 |

1. Subclones of TGH-01.
2. Clone containing only the 5' portion of TO cDNA.

The various lambda libraries were screened by plating approximately 30,000 plaques on LB agar on 150 mm petri dishes. Duplicate lifts were made on Nitrocellulose BA-85. The membranes were screened by labeling with the probes listed, labeled with 32P by nick translation. Areas of coincident positive signal were scraped from the plate and re-screened at a lower plaque density. The lambda inserts were subcloned into Bluescript.

The entire expressed portion and regulatory sequences of the human TO gene (TD02) has also been sequenced using the Sanger method. The sequence is depicted by FIGS. 8-1, 8-2 and 8-3. The numbering starts at −1,652 bases from the start site of the transcribed portion of the TD02 gene and then extends from +1. There is a promoter CATAA (TATA) box at −24 and a second minor TATA box at −213. There is a promoter homologous to the CAAT box at −74. The sequence is CTAAG, identical to the sequence in the rat trytophan oxygenase gene. In comparison to the rat sequence there is an insert of DNA starting at −293 and extending to −1,957. There is a glucocorticoid response element (GRE) at −1,510 homologous to the second rat GRE.

Within the insert there are a series of GTT repeats starting at −823. Since part of the GRE consensus sequence is GTTCTT, this GTTGTT repeat may serve as a GRE-like element.

Figure 9:
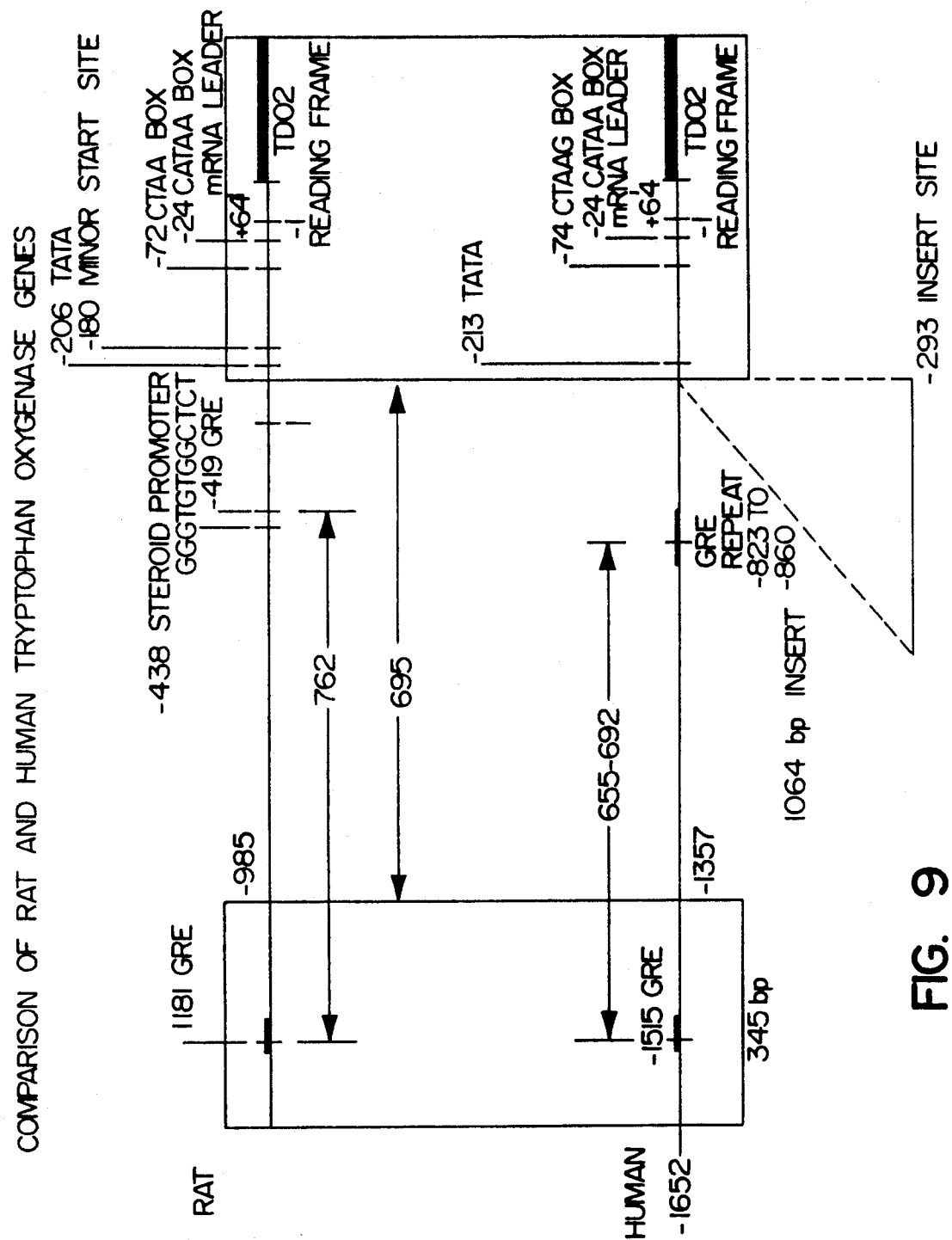
FIG. 9 is a diagramatic comparison of the sequence of the rat versus the human TD02.

FIG. 9 is a diagramatic comparison of the sequence of the rat versus the human TD02. The regions of homology are shaded. The site of the DNA insert is clearly shown.

FIG. 10 is a comparison of the amino acid sequence of the rat (Maezono, K., et al., Deduced primary structure of rat tryptophan-2,3-dioxygenase, *Biochem. Biophys. Res. Comm.* 170:176–181 (1990)) versus the human tryptophan oxygenase gene. This comparison shows that there is an 88% homology between the two sequences and clearly identifies the human sequence as tryptophan oxygenase.

In addition to the expressed and regulatory regions, some of the TD02 introns have also been sequenced. These are shown by FIGS. 11-1, 11-2 and 11-3 which also illustrates some of the synthetic oligomers (shown by lines through the sequence) used for the PCR amplification of specific regions of TD02 and are useful for the diagnosis of disease producing mutations of the TD02 gene. The numbers indicate the name of the synthetic oligomer. The position of the number indicates the direction the oligomer is pointing (i.e., 3' or 5').

Figure 12:
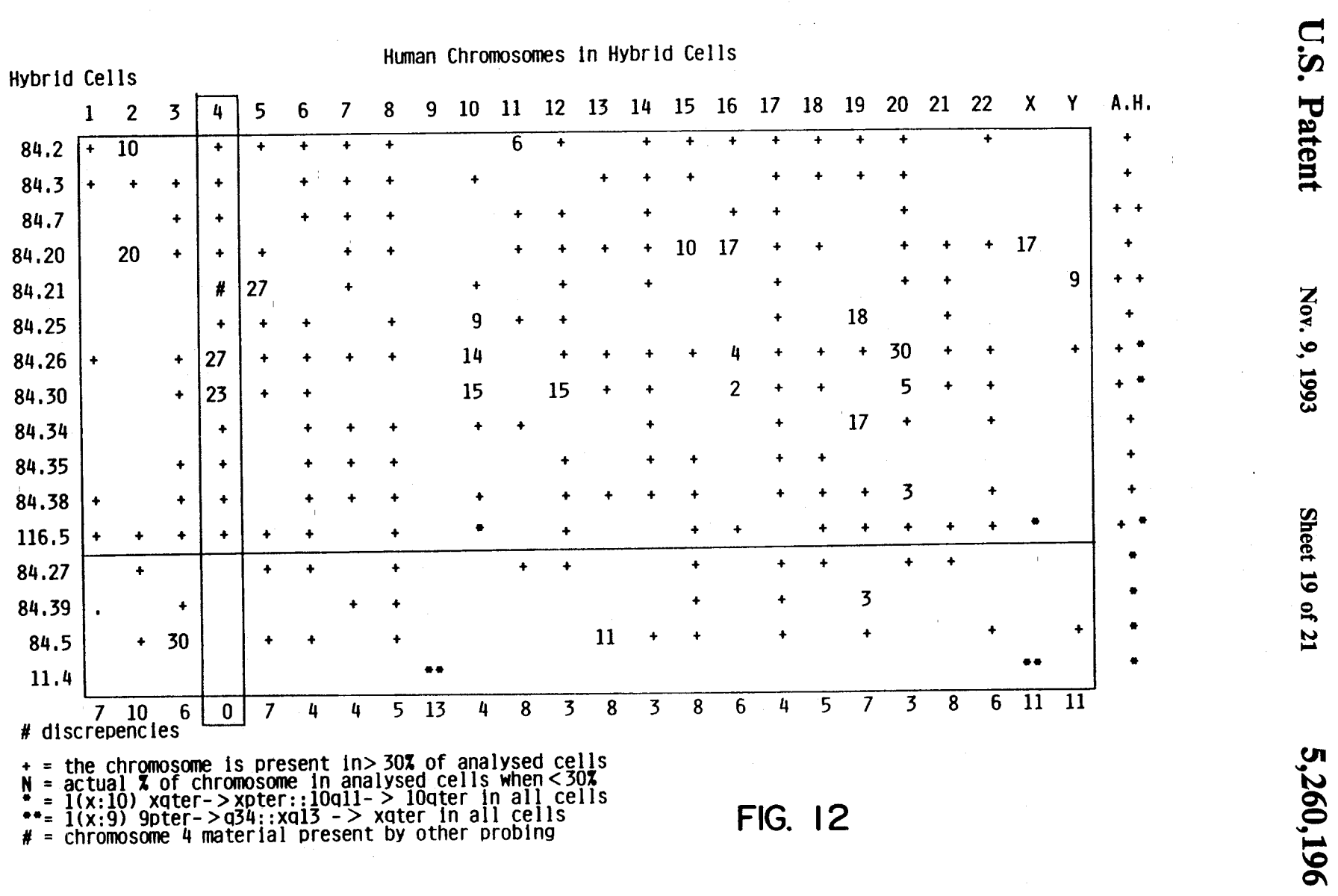
Figure 13:
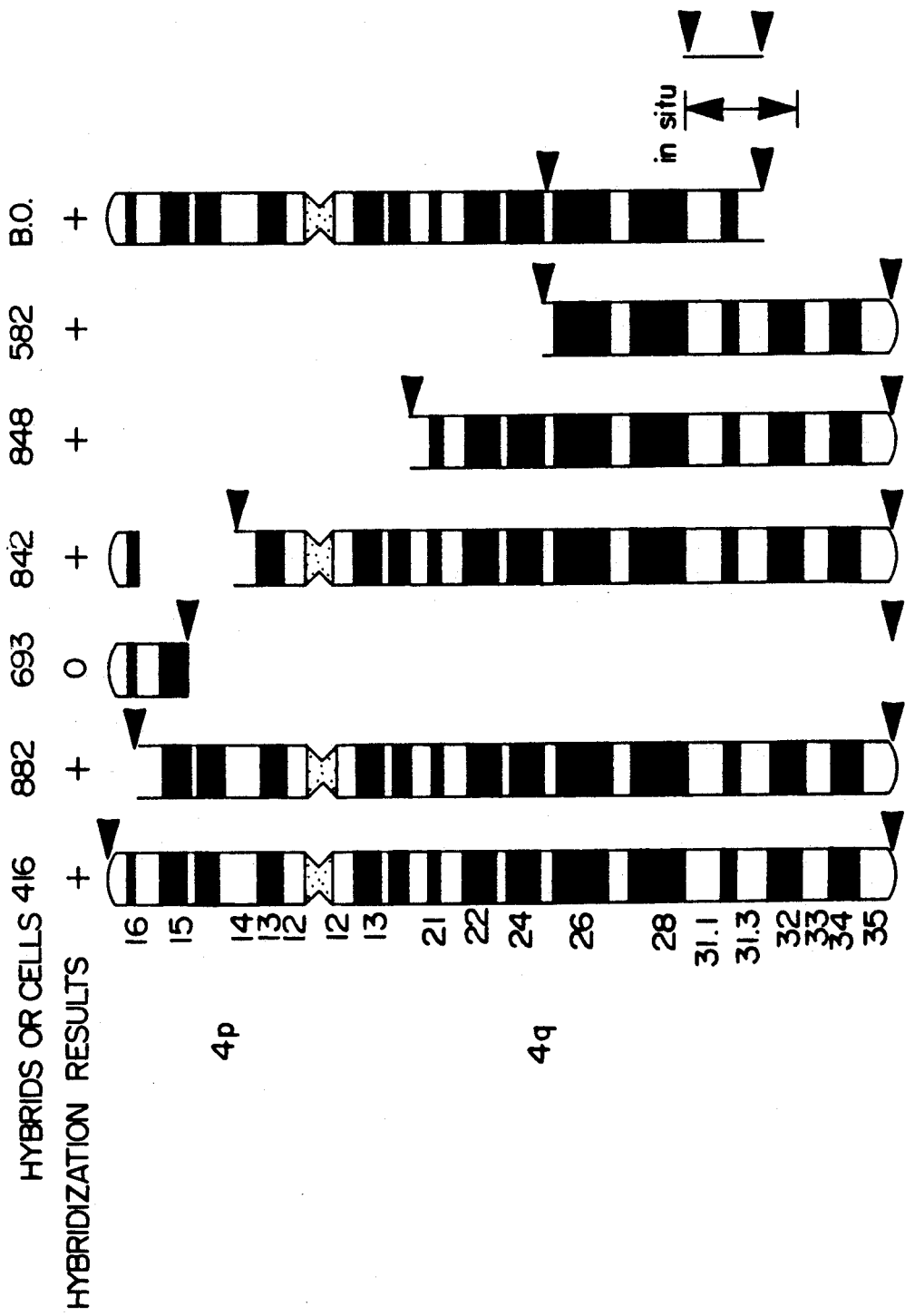
FIG. 13 depicts the chromosomal location of the human TD02 gene to 4q31.

The HT03 clone was used in the hybridization of rodent-human cell hybrids and for in situ hybridization studies to identify the chromosomal location of the human TD02 gene (see FIGS. 12 and 13). These studies indicated the human TD02 gene is in chromosome band 4q31 (see Comings, D. E., Muhleman, D., Dietz, G. W. and Donlon, T. "Human tryptophan oxygenase localized to 4q31: Possible implications for human behavioral disorders. *Genomics* 9:301–308 (1991)).

PROOF THAT MUTATIONS OF TD02 CAUSE TS AND TS RELATED BEHAVIORS

The connection between mutations affecting the structural integrity of tryptophan oxygenase and Tourette syndrome has been proven by an assay of tryptophan oxygenase in lysates of red blood cells from controls and patients with Tourette syndrome (TS), using tryptophan, heme and oxygen as substrates. This assay is performed by detecting the rate of production of kynurenine in a double beam recording U.V. spectrophotometer, over time. The rate is determined using the linear portion of the curve. The mean rate of production of kynurenine in controls can thus be compared to the rate of production in patients with TS. The results are shown in FIG. 14. Twenty-five TS patients were assayed and all had TD02 enzyme levels in the range of 150% of normal. Thirteen control patients were assayed. One of 13 controls had elevated TD02 levels, verifying the high carrier frequency of the mutant TD02 gene, as proposed by the applicant. See, Comings, D. E., Himes, J. and Comings, B. G. "An epidemiological study of Tourette syndrome in a single school district", *J. Clin. Psychiatry* 51:463–469 (1990).

ELECTROPHORESIS OF MUTANT TD02 IN TS

Electrophoresis of the red blood cell lysate, in conjunction with assay in the gel for the TD02 enzyme activity, showed that the increase in TD02 activity was due to a mutation of the TD02 gene, and not due to indirect causes such as an increase in blood steroid levels. The controls (with a normal range of enzyme activity) had a single band with low levels of activity (FIG. 15). Since TD02 is a tetrameric protein, this is interpreted as all four monomeric units being normal.

Twenty of the twenty five patients were heterozygotes for the TD02 mutation and had three bands (FIG. 15). This is interpreted as a pair of normal dimers for the normal enzyme, a set of mutated dimers and normal dimers, and a set of mutated dimers.

Five of twenty-five TS patients were homozygous for the mutant TD02 had a single band (FIG. 15). This is interpreted as a pair of mutant dimers.

In TD02 two subunits or monomers are bound to a single heme forming dimer. The organization of TD02 into two dimers accounts for presence of three and only three bands by electrophoresis.

The heterozygous TS patients had the TS spectrum of psychiatric disorders on either the maternal or paternal side of the family. The homozygous TS patients had the spectrum of TS related behaviors on both sides of the family.

These results teach that mutations of the TD02 gene result in elevated activity of TD02 and are causative of TS in either heterozygous or homozygous dosage and establish the claimed relationship between genetic mutations of this gene and TS and TS associated behaviors.

This discovery is unique in its demonstration that mutations of TD02 are causative in TS and its TS associated disorders or TS spectrum disorders. Prior suggestions of a link between tryptophan oxygenase (tryptophan pyrrolase) and a single specific psychiatric disorder, depression (Mangoni et al) assumed the increased levels of TD02 were due to a nongenetic cause, i.e., the well known inducibility of TD02 by steroids (hydrocortisone and others). Thus this old proposal was:

stress→increased adrenal steroids→increased TD02→depression. No mention of genetic mutations, the important and unique aspect of this invention, was made.

Our unique claim and demonstration is that:

genetic mutations→increased TD02 activity→defective serotonin metabolism→many psychiatric disorders (TS and TS spectrum disorders).

The distinction is critical. If, as previously proposed, increases in the activity of TD02 in depression were secondary to elevated adrenal steroid levels, there would be no need to attempt to identify mutations of the TD02 gene since the basic cause of depression would lie elsewhere. The present invention, demonstration and teaching that genetic mutations of the TD02 gene are the primary and basic cause of TS and TS associated behaviors, is new and unique, and allows specific tests to be performed to aid in the rapid diagnosis and treatment of TS and TS associated behaviors.

I claim:

1. A method for the diagnosis of Tourette syndrome, Tourette syndrome associated disorders and Tourette spectrum disorders which comprises:
   (i) providing a lysate of red blood cells of
      (a) a patient suspected of having Tourette syndrome, Tourette syndrome associated disorders or Tourette spectrum disorders and of
      (b) a control,
   (ii) comparing the level of kynurenine in said lysates, and
   (iii) diagnosing said patient as afflicted with Tourette syndrome, Tourette syndrome associated disorders or Tourette spectrum disorders if the kynurenine level in said patient's red blood cell lysate is greater than the kynurenine level in said control lysate.

* * * * *